United States Patent [19]
Walker et al.

[11] Patent Number: 5,470,723
[45] Date of Patent: Nov. 28, 1995

[54] DETECTION OF MYCOBACTERIA BY MULTIPLEX NUCLEIC ACID AMPLIFICATION

[75] Inventors: George T. Walker; James G. Nadeau, both of Chapel Hill; Patricia A. Spears; Colleen M. Nycz, both of Raleigh; Daryl D. Shank, Durham; James L. Schram, Nightdale; Stewart R. Jurgensen, Raleigh, all of N.C.

[73] Assignee: Becton, Dickinson and Company, Franklin Lakes, N.J.

[21] Appl. No.: 111,076

[22] Filed: Aug. 24, 1993

Related U.S. Application Data

[63] Continuation-in-part of Ser. No. 73,197, Jun. 4, 1993, Pat. No. 5,422,252, Ser. No. 58,648, May 5, 1993, Pat. No. 5,348,980, and Ser. No. 60,842, May 11, 1993, abandoned.

[51] Int. Cl.$^6$ .............................. C12Q 1/68; C12P 19/34; C07H 15/12; C07H 17/00
[52] U.S. Cl. ................... 435/91.2; 435/6; 536/24.32; 536/24.33; 935/17; 935/77; 935/78
[58] Field of Search ............... 435/6, 91.2; 536/24.32, 536/24.33; 935/77, 78, 17

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 5,213,961 | 5/1993 | Bunn et al. | 435/6 |

FOREIGN PATENT DOCUMENTS

| | | |
|---|---|---|
| 0364255 | 4/1990 | European Pat. Off. |
| 0525882A1 | 2/1993 | European Pat. Off. |
| WO92/11273 | 7/1992 | WIPO |
| WO93/02215 | 2/1993 | WIPO |

OTHER PUBLICATIONS

G. T. Walker, et al. "Strand displacement amplification—an isothermal in vitro DNA amplification technique" *Nuc. Acids Res.* 20:1691–1696 (1992).

G. T. Walker, et al. "Isothermal in vitro amplification of DNA by a restriction enzyme/DNA polymerase system" *Proc. Natl. Acad. Sci. USA* 89:392–396 (1992).

P. R. Mueller, et al. "In Vivo Footprinting of a Muscle Specific Enhancer by Ligation Mediated PCR" *Science* 246:780–246 (1989).

*Primary Examiner*—Mindy B. Fleisher
*Attorney, Agent, or Firm*—Donna R. Fugit

[57] ABSTRACT

Primers and methods for adapter-mediated multiplex amplification of the IS6110 insertion element of *Mycobacterium tuberculosis* (M.tb) and the 16S ribosomal gene of *Mycobacterium tuberculosis*, useful for simultaneously detecting and/or identifying species of the *M. tuberculosis* complex and other clinically relevant Mycobacterium species. Multiplex Strand Displacement Amplification (SDA) is used in a single amplification reaction which is capable of simultaneously identifying *M. tuberculosis* and providing a screen for substantially all of the clinically relevant species of Mycobacteria. Also disclosed are methods for adapter-mediated multiplex amplification of multiple target sequences and a single internal control sequence for determination of sample efficacy or quantitation of the targets. In a preferred embodiment, an internal control sequence is included in the amplification reaction and coamplified with the IS6110 ant 16S target sequences as an indication of sample amplification activity or to quantitate the initial amount of target sequences in the sample.

31 Claims, 4 Drawing Sheets

FIG-2

```
            Bg1                                              Sg                    Dg,Dff         Ag              Bg2
         ┌─────┐                                          ┌─────┐                ┌─────┐       ┌─────┐         ┌─────┐
    507→ CGGAATTACTGGGCGTAAAGAGCTCGTAGGTGGTTTGTCGCGTTGTTCGTGAAATCTCACGGCTTAACTGTGAGCGTGCGGGCGATACGGGCAGACT ←603
```

| | Bg1 | Sg | Dg,Dff | Ag | Bg2 |
|---|---|---|---|---|---|
| M. TUBERCULOSIS | | | | | |
| M. FORTUITUM | | | A | G | |
| M. CHELONAE | | | A | G | |
| M. TERRAE | | | A | G | |
| M. FLAVESCENS | | C | A C | G | |
| M. XENOPI | C C | | G GC A | G | |
| M. GENAVENSE N | | | A CGGG | CC CG | G |
| C. DIPHTHERIAE | | C CT | TC GG | TC G | A |
| C. XEROSIS | M | C CT | TC GG | CC G | A |
| R. EQUI | M | C C | A TGG C | CCYA T | T AC |
| N. ASTEROIDES T | | C A | A T C | CCCA T | T AC |
| N. OTITIDIS/CAVIARUM T | | C A C | A GTG A C | C C | NT |
| S. GINSEUS | T | C GAT | G C GG | CCC GTC | N |
| S. ALBUS | T | C GAT | G C GG T | CCC GTC | ATT |
| A. ISRAELII T T | G TT | NA C GAA T | TN N | CC | TAG ATT |
| P. ACNES T T | G | GA C GAA T | TGG | CC | G TT TTT |
|  |  |  |  |  | TT TTT |

DETECTION OF MYCOBACTERIA BY MULTIPLEX NUCLEIC ACID AMPLIFICATION

This application is a continuation-in-part of patent application U.S. Ser. No. 08/073,197 filed Jun. 4, 1993, now U.S. Pat. No. 5,422,252, a continuation-in-part of patent application U.S. Ser. No. 08/058,648 filed May 5, 1993, now U.S. Pat. No. 5,348,980, and a continuation-in-part of patent application U.S. Ser. No. 08/060,842 filed May 11, 1993, now abandoned, the disclosures of which are hereby incorporated by reference.

FIELD OF THE INVENTION

The present invention relates to nucleic acid amplification and detection and/or identification of microorganisms using nucleic acid amplification.

BACKGROUND OF THE INVENTION

In vitro nucleic acid amplification techniques have provided powerful tools for detection and analysis of small amounts of nucleic acids. The extreme sensitivity of such methods has lead to attempts to develop them for diagnosis of infectious and genetic diseases, isolation of genes for analysis, and detection of specific nucleic acids as in forensic medicine.

In general, diagnosis and screening for specific nucleic acids using nucleic acid amplification techniques has been limited by the necessity of amplifying a single target sequence at a time. In instances where any of multiple possible nucleic acid sequences may be present (e.g., infectious disease diagnosis), performing multiple separate assays by this procedure is cumbersome and time-consuming. U.S. Pat. Nos. 4,683,195; 4,683,202 and 4,800,159 describe the PCR. Although these inventors state that multiple sequences may be detected, no procedure for amplifying multiple target sequences simultaneously is disclosed. When multiple target sequences are amplified, it is by sequentially amplifying single targets in separate PCRs. In fact, when multiple pairs of primers directed to different target sequences are added to a single PCR, the reaction produces unacceptably high levels of nonspecific amplification and background. An improvement on the PCR which reportedly allows simultaneous amplification of multiple target sequences is described in published European Patent Application No. 0 364 255. This is referred to as multiplex DNA amplification. In this method, multiple pairs of primers are added to the nucleic acid containing the target sequences. Each primer pair hybridizes to a different selected target sequence, which is subsequently amplified in a temperature-cycling reaction similar to PCR. Adaptation of PCR to footprinting is taught by P. R. Mueller and B. Wold (1989. *Science* 246, 780–786). For footprinting, a common oligonucleotide sequence is ligated to the unique end of each fragment of the footprint ladder. The fragments are simultaneously amplified using a primer complementary to the common sequence and a primer complementary to the known sequence of the fixed end.

In most cases, nucleic acid amplification techniques have been used to produce qualitative results in diagnostic assays. However, there has been great interest in developing methods for nucleic acid amplification which are not only capable of detecting the presence or absence of a target sequence, but which can also quantitate the amount of target sequence initially present. Internal control sequences have been used in the PCR in an attempt to produce such quantitative results. Parent application U.S. Ser. No. 08/058,648 discloses internal controls sequences useful in isothermal nucleic acid amplification reactions for quantitating target sequence as well as determining the amplification activity of the sample (i.e., efficacy—whether or not the sample inhibits the amplification reaction, thus producing a false negative result).

Certain PCRs which employ internal controls select internal control sequences which can be amplified by the same primers as the target sequence. See, for example, WO 93/02215 and WO 92/11273. In the PCR, the amplified target and control sequences may distinguished by different fragment lengths as the rate of the PCR is known to be relatively unaffected by the length of the target and does not significantly affect amplification efficiency. EP 0 525 882 describes a method for quantifying a target nucleic acid in a Nucleic Acid Sequence Based Amplification (NASBA) reaction by competitive amplification of the target nucleic acid and a mutant sequence. The method is performed with a fixed amount of sample and a dilution series of mutant sequence. The analysis involves determining the amount of added mutant sequence which reduces the signal from the target sequence by 50%, i.e., the point at which the mutant sequence and target sequence are present in equal amounts. To produce accurate quantification, the amplification reactions described in EP 0 525 882 must be allowed to continue until at least one of the reagents is essentially exhausted, i.e., into the post-exponential phase of the reaction where competition for limited reagents can occur. Furthermore, the calculations are accurate only when two reactions are competing for reagents—the target amplification and the mutant sequence amplification. The results are therefore not reliable when a third reaction, such as background amplification, is occurring. As essentially all amplification reactions include some degree of background amplification, the EP 0 525 882 quantifying method is only accurate for a high level of target sequence. At low target levels, competing background amplification reactions would significantly interfere with the accuracy of the calculations. Because it relies on amplifying various dilutions of the mutant sequence with the target, the EP 0 525 882 method is also susceptible to tube-to-tube variations in the amount of mutant and target sequence. Even small differences in the amount of target sequence or slight inaccuracies in the dilutions of mutant sequence between tubes are exponentially amplified in the subsequent amplification reaction and are reflected in the quantification calculations.

In contrast, the method of U.S. Ser. No. 08/058,648 does not require competition between control and target sequences for reagents nor does it require that the reaction go into the post-exponential phase. It is accurate in both the exponential and post-exponential phases of the amplification reaction. The ratio of target/control sequence is therefore not adversely affected by background amplification reactions which may be occurring and remains the same regardless of the extent of background reaction. The result can therefore be obtained earlier in the amplification reaction and variability is reduced by the use of a single target/control coamplification reaction rather than a series of reactions.

Previously reported multiplex nucleic acid amplification methods require a separate internal control sequence matched to each target to be amplified because each target is amplified using a different pair of primers (i.e., a control sequence for each primer pair). Prior to the present invention it was not possible to use a single internal control sequence to monitor or quantitate multiple targets in multiplex nucleic acid amplification reactions. It is therefore a feature of the instant adapter-mediated multiplex amplification methods that the single pair of primers required for multiplex amplification makes it possible for the first time to use a single internal control sequence to monitor or quantitate amplification of the multiple targets.

The Mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. Many of these new cases are related to the AIDS epidemic, which provides an immune compromised population which is particularly susceptible to infection by Mycobacteria. Other mycobacterial infections are also increasing as a result of the increase in available immune compromised patients. *Mycobacterium avium, Mycobacterium kansasii* and other non-tuberculosis mycobacteria are found as opportunistic pathogens in HIV infected and other immune compromised patients.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing Mycobacterial infections to less than a week, preferably to about one day. Oligonucleotide probe based assays such as Southern hybridizations or dot blots are capable of returning a rapid result (i.e., in one day or less). Assays based on amplification of nucleic adds may provide even more rapid results, often within hours. For diagnosis of Mycobacterial infections such methods would require an oligonucleotide probe or primer which is specific for the genus of Mycobacteria or specific for a particular mycobacterial species if specific identification of the organism is desired.

SUMMARY OF THE INVENTION

It has now been discovered that the primers disclosed in U.S. Ser. No. 08/073,197 to exemplify adapter-mediated multiplex amplification of the IS6110 insertion element of *Mycobacterium tuberculosis* (M.tb) and the 16S ribosomal gene of *Mycobacterium tuberculosis* are also useful for simultaneously detecting and/or identifying species of the *M. tuberculosis* complex and other clinically relevant Mycobacterium species by nucleic acid amplification. The inventive methods use multiplex Strand Displacement Amplification (SDA) in a single amplification reaction which is capable of simultaneously identifying *M. tuberculosis* and providing a screen for substantially all of the clinically relevant species of Mycobacteria. SDA is capable of amplifying two target DNA sequences $10^8$-fold during a single incubation at a constant temperature.

In a particularly preferred embodiment, the amplification reaction further includes an internal control sequence as described in U.S. Ser. No. 08/058,648. This internal control sequence is co-amplified with the two target sequences in a multiplex amplification protocol employing a single pair of amplification primers for simultaneous amplification of the IS6110, 16S and internal control targets (triplex amplification). In this embodiment the assay, in a single amplification reaction, provides means for quantitating target or determining sample amplification activity and detecting/identifying clinically relevant Mycobacteria which may be present. The simultaneous amplification of genus- and species-specific Mycobacterium sequences with a single internal control sequence exemplifies the broader applicability of the disclosed methods for adapter-mediated multiplex amplification of multiple targets and a single internal control sequence using the same primer pair.

DESCRIPTION OF THE DRAWINGS

FIG. 2 shows sequence alignments for the Mycobacterium genus target sequence in the 16S ribosomal genes of various Mycobacterium species, including illustration of the primer binding sites.

DETAILED DESCRIPTION OF THE INVENTION

Figure 1:
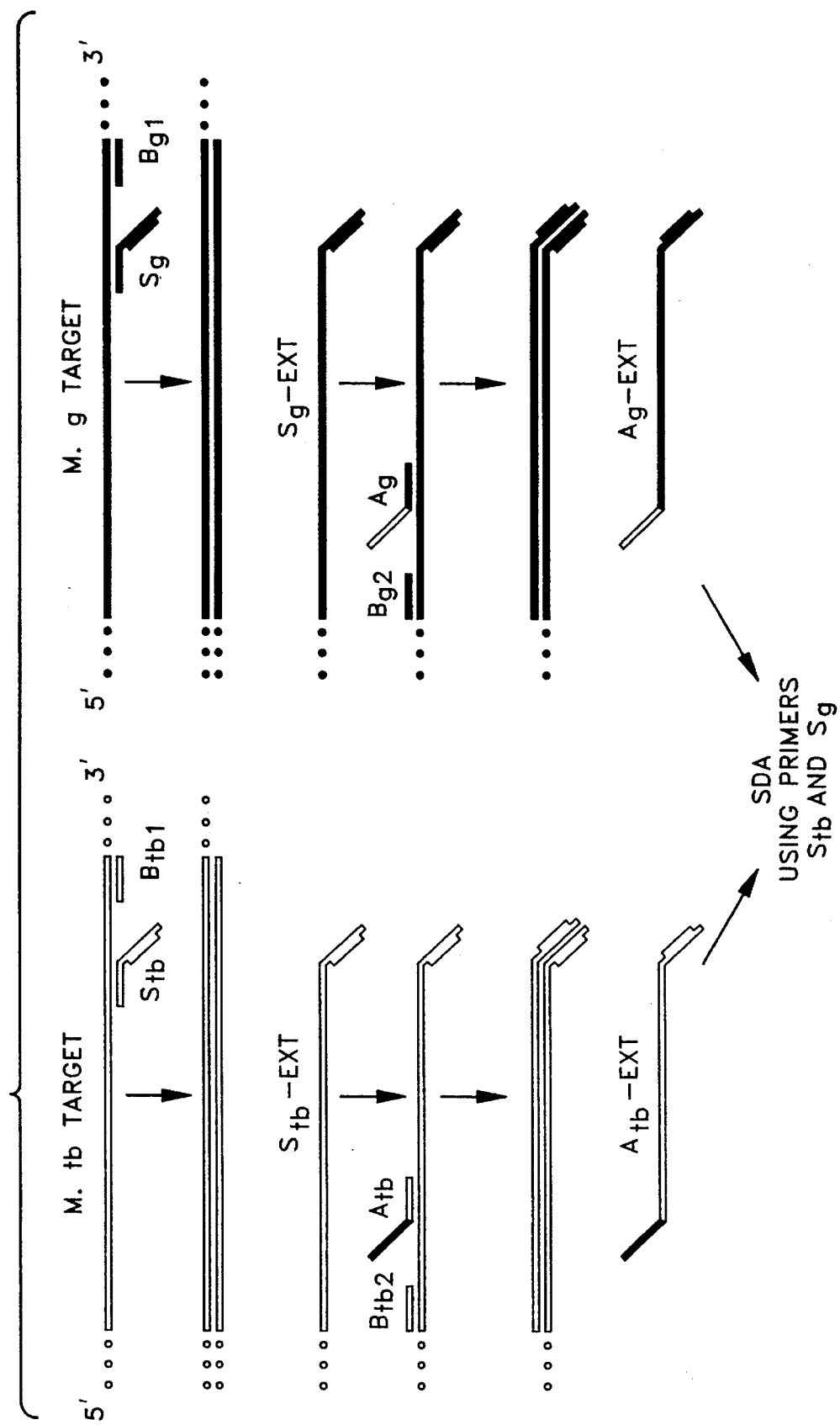
FIG. 1 is a diagram illustrating the method of the invention used for coamplification of two target sequences in Example 1, Example 2 and Example 3.

The present invention provides methods for simultaneous amplification of multiple target sequences by sequence specific hybridization of primers, particularly by SDA (multiplex SDA). The methods use a single pair of amplification primers or a single SDA amplification primer to coamplify the multiple target sequences. This is accomplished by appending a defined adapter sequence to the targets and amplifying by primer extension. The inventive methods are referred to herein as "adapter-mediated multiplexing." This is in contrast to "conventional multiplexing" in which multiple pairs of target-specific primers are used to coamplify the multiple targets without addition of adapter sequences.

The following terms are defined herein as follows:

An amplification primer is a primer for amplification of a target sequence by sequence specific hybridization. For SDA, the 3' end of the amplification primer (the target binding sequence) hybridizes at the 3' end of the target sequence and comprises a recognition site for a restriction enzyme near its 5' end. The recognition site is for a restriction enzyme which will nick one strand of a DNA duplex when the recognition site is hemimodified, as described by Walker, et al. (1992. *PNAS* 89, 392–396 and *Nucleic Acids Res.* 20, 1691–1696) and in U.S. Ser. No. 07/819,358, filed Jan. 9, 1992 (the disclosure of which is hereby incorporated by reference). A hemimodified recognition site is a double stranded recognition site for a restriction enzyme in which one strand contains at least one derivatized nucleotide which prevents cutting of that strand by the restriction enzyme. The other strand of the hemimodified recognition site does not contain derivatized nucleotides at the cleavage site and is nicked by the restriction enzyme. The preferred hemimodified recognition sites are hemiphosphorothioated recognition sites for the restriction enzymes HincII, HindII, AvaI, NciI and Fnu4HI. For the majority of the SDA reaction, the amplification primer is responsible for exponential amplification of the target sequence.

An adapter primer is an oligonucleotide which has a sequence at its 3' end (the target binding sequence) for hybridizing to the target sequence. At the 5' end of the adapter primer is an adapter sequence. The adapter sequence may be a sequence which is substantially identical to the 3' end of one of the amplification primers or it may be any defined sequence for which amplification primers with complementary target binding sequences can be prepared.

A bumper primer is a primer which anneals to a target sequence upstream of either an adapter or amplification primer, such that extension of the bumper primer displaces the downstream primer and its extension product. Extension of bumper primers is one method for displacing the extension products of adapter and amplification primers, but heating is also suitable.

Identical sequences will hybridize to the same complementary nucleotide sequence. Substantially identical sequences are sufficiently similar in their nucleotide sequence that they also hybridize to the same nucleotide sequence.

The terms target or target sequence refer to nucleic acid sequences to be amplified. These include the original nucleic acid sequence to be amplified and its complementary second strand (prior to addition of adapter sequences), either strand of an adapter-modified copy of the original sequence as described herein, and either strand of a copy of the original sequence which is an intermediate product of the reactions in which adapter sequences are appended to the original sequence.

Species-specific amplification of a target sequence refers to amplification of a target sequence in the species of Mycobacteria classified as members of the *Mycobacterium tuberculosis* complex, but little or no amplification in non-M.tb complex Mycobacteria.

Genus-specific amplification of a target sequence refers to amplification of a target sequence in substantially all of the clinically relevant species of Mycobacteria, but little or no amplification in similar non-Mycobacterium species.

In the adapter-mediated multiplexing of the invention, adapter sequences are appended to the ends of target sequences by means of adapter primers and a series of extension and strand displacement steps. FIG. 1 illustrates one embodiment of the present invention in which two target sequences are co-amplified using a single pair of amplification primers. One of the two target sequences is M.tb complex-specific (e.g., IS6110) and the other target sequence is specific for all genera of Mycobacterium (M.g— e.g., the 16S gene). Modification of only one strand of each target sequence is illustrated for clarity. In this embodiment, one end of each target strand is modified by appending to it a sequence substantially identical to a terminal segment of the other target. The other end of each target strand remains unmodified and retains its original complementarity to one member of the amplification primer pair. As detailed below, the resulting modified targets can then both be amplified by a single pair of amplification primers, one member of the pair being complementary to one of the two original target sequences and the other member of the pair being complementary to the other of the two original target sequences. For the first (M.tb complex-specific) target (M.tb Target), an M.tb-specific amplification primer ($S_{tb}$) is hybridized to the 3' end of the target sequence and extended with polymerase. The nicking enzyme recognition site of the amplification primer is depicted in FIG. 1 as a raised portion of the primer.

The resulting extension product is displaced by extension of a bumper primer ($B_{tb1}$) which hybridizes to the target upstream from $S_{tb}$. The displaced $S_{tb}$ extension product ($S_{tb}$-ext) is hybridized to an adapter primer ($A_{tb}$) which binds to $S_{tb}$-ext at the 3' end of the complement of the original target sequence. The 5' end of $A_{tb}$ comprises the adapter sequence (solid portion), which is substantially identical to the target binding sequence at the 3' end of $S_g$, an amplification primer which specifically binds to the second, Mycobacterium genus-specific target (M.g Target). Extension of $A_{tb}$ and displacement of the $A_{tb}$ extension product ($A_{tb}$-ext) produces a single stranded copy of the M.tb target sequence with a nicking enzyme recognition site and the M.tb target sequence at its 3' end and the $S_g$ target binding sequence at its 5' end.

The second target (M.g Target) is treated similarly, first binding and extending an M.g-specific amplification primer ($S_g$), then hybridizing an adapter primer ($A_g$) to the extension product ($S_g$-ext). $S_g$ hybridizes to the M.g target at a 3' terminal segment of the target which is complementary to both the target binding sequence of $S_g$ and the adapter sequence of $A_{tb}$. The 3' end of adapter primer $A_g$ hybridizes at the 3' end of the complement of the original target and the 5' end of $A_g$ (open portion) is substantially identical to the target binding sequence of $S_{tb}$. Extension and displacement of the $A_g$ extension product ($A_g$-ext) produces a copy of the second target sequence with a nicking enzyme recognition site (raised portion) and the M.g target sequence at its 3' end and the $S_{tb}$ target binding sequence at its 5' end. The two adapter-modified copies of the target sequences are amplifiable by SDA using only the $S_{tb}$ and $S_g$ amplification primers already present in the reaction. To begin SDA, $A_{tb}$-ext and $A_g$-ext hybridize to their respective amplification primers, which are extended to produce the complement of the modified strand (i.e., extension of $S_{tb}$ on the M.tb modified strand and extension of $S_g$ on the M.g modified strand), including the complement of the adapter sequence at the 3' end. After nicking and displacement, the amplification primer of the opposite target can then bind to the 3' end of this extension product (i.e., $S_g$ to the M.tb-derived strand and $S_{tb}$ to the M.g-derived strand) and is extended to produce a fragment with a nicking enzyme recognition site at each end. This fragment is amplified by conventional SD as described by Walker, et al., supra.

The double stranded reaction products which are produced after displacement of $A_{tb}$-ext and $A_g$-ext may also participate in a reaction loop which generates additional copies of $A_{tb}$-ext and $A_g$-ext. Nicking the restriction enzyme recognition site of the bottom strand, extending with polymerase and displacing the bottom strand produces targets which are similar to $S_{tb}$-ext and $S_g$-ext but with half of a restriction enzyme recognition site at the 5' end. The adapter primers can bind to these fragments and can be extended and displaced to produce additional copies of $A_{tb}$-ext and $A_g$-ext (also with half of a restriction enzyme recognition site at the 5' end) which enter the SDA reaction cycle as described above.

FIG. 1 depicts the generation of modified targets from only one of the two complementary strands normally present fix each target sequence. Processes similar to those shown also originate from the second strand of each target. In the case of the second strand, however, the order of binding and extension of the primers is reversed. The adapter primers first bind directly to the target second strand and are extended on that template. After its subsequent displacement, the resulting adapter extension product hybridizes to the amplification primer, which is in turn extended and displaced to give a product containing the original second strand target sequence with a recognition site for a nicking restriction enzyme at its 5' end and a sequence complementary to the adapter sequence at its 3' end. This modified fragment enters conventional SDA amplification by binding and extension of the amplification primer specific for the opposite target (i.e., $S_g$ binds to the M.tb-derived strand and $S_{tb}$ binds to the M.g-derived strand), producing a fragment for each target second strand with a nicking enzyme recognition site at each end.

All of the reaction steps involved in appending the adapter sequences and amplifying the target may occur concurrently in a single reaction mixture. That is, once adapter sequences are appended to a target molecule, amplification of that target molecule can take place within the same reaction mixture prior to appending of the adapter sequences to any other target molecules present and without isolation of the modified target. Reaction conditions for the methods of the invention are essentially as described by Walker, et al., supra, for SDA, with some modifications. First, the initial reaction mix contains both the amplification primers and the adapter primers as well as the target DNA. In addition, the amplification primers are preferably present in about 10-fold excess over the adapter primers and about 20-fold excess over the bumper primers. The concentration of bumper primers is not critical, but will generally be less than the concentration used in conventional SDA. However, like conventional SDA, the nicking restriction enzyme and exo⁻ klenow polymerase are added after heat denaturation of the target DNA and annealing of the primers. After denaturation of the target DNA, annealing of the primers and addition of polymerase, the processes of appending the adapter sequences and amplification proceed automatically in a single reaction mixture without further intervention by the practitioner. That is, after adapter sequences are appended, a modified target sequence automatically enters the SDA reaction cycle.

The complete nucleotide sequence of the IS6110 insertion element has been described by Thierry, et al. (1990. *Nucleic Acids Res.* 18, 188). The methods of the invention provide primers which amplify a target sequence within the IS6110 insertion element which is present in the species of the Mycobacterium complex (*M. tuberculosis, M. bovis, M. bovis* BCG, *M. africanum* and *M. microti*). The primers are complementary to nucleotides 972–984 of IS6110 and support little or no amplification of target in Mycobacterium species other than the M.tb complex or in non-Mycobacterium species. These primers are defined herein as species-specific primers.

Alignment of the 16S ribosomal genes of various Mycobacterium species, as shown in FIG. 2, was used to design genus-specific primers for nucleic acid amplification which would amplify a target in substantially all of the clinically relevant species of Mycobacteria but not in non-Mycobacterium species. The selected *M. tuberculosis* sequence at nucleotide positions 507–603 is identical to the sequences in *M. bovis, M. bovis* BCG, *M. avium, M. intracellulare, M. kansasii, M. gastri, M. paratuberculosis, M. malmoense, M. szulgai, M. gordonae, M. leprae, M. ulcerans, M. asiaticum* and *M. scrofulaceum*. For some species in the sequence database, an undetermined nucleotide is listed at position 587 or 588, but neither of these positions involve primer binding. *M. terrae, M. chelonae, M. fortuitum* and our strain of *M. marinum* vary from this common sequence at three nucleotide positions. The sequence of our strain of *M. marinum* was unexpected, as the GENBANK sequence for this organism was reportedly identical to *M. bovis*, not *M. terrae. M. flavescens, M. xenopi* and *M. genavense* exhibit more extensive sequence variance. This target sequence diverges significantly from the M.tb sequence in organisms which are otherwise generally similar to Mycobacteria. In spite of the sequence variability among Mycobacteria, however, it was found that the primers designed to amplify the target sequence as shown in FIG. 2 specifically amplified a target present in the clinically relevant genera of Mycobacteria but not in other similar non-Mycobacterium species. These primers are defined herein as genus-specific primers.

Simultaneous amplification of the M.tb species-specific IS6110 sequence and the genus-specific 16S sequence in a multiplex SDA reaction allows rapid detection and/or identification of M.tb organisms and other clinically relevant Mycobacterium species in a single reaction. Detection of amplified IS6110 and 16S targets is indicative of the presence of an *M. tuberculosis* complex organism in the sample. Detection of only 16S targets indicates the presence of non-M.tb complex Mycobacteria. As results can be obtained within a day using nucleic acid amplification methods, it is no longer necessary to wait six weeks for culture results before reaching a decision that a sample is negative for clinically relevant Mycobacteria.

In a first embodiment, IS6110 and 16S target sequences are co-amplified by adapter-mediated multiplex SDA using the genus-specific and species-specific primers of the invention. In an alternative preferred embodiment, the adapter-mediated multiplex SDA reaction further includes an internal control sequence as, described in U.S. Ser. No. 08/058, 648. The preferred internal control sequence for use with the genus-specific and species-specific primers of the following Examples is (SEQ ID NO: 12). SEQ ID NO: 12 contains the core sequence of SEQ ID NO: 1 of U.S. Ser. No. 08/058,648 and an amplification primer binding sequence at each end to facilitate co-amplification using a single pair of primers as taught in U.S. Ser. No. 08/073,197. The amplification primer binding sequences of the internal control sequence are complementary to the target binding sequences of the amplification primers.

It will be apparent to one skilled in the art from the foregoing disclosure that either the IS6110 or 16S sequences may be amplified alone in a conventional SDA reaction. For example, for M.tb detection only the 16S sequence may be amplified according to Walker, et al. using $S_g$ and $S_{tb}$ with the $A_g$ adapter primer. Alternatively, when only genus-specific detection is desired, the 16S sequence may be amplified using $S_g$ and a $A_g$ modified to function as an amplification primer, i.e., replacing the M.tb adapter sequence with a HincII restriction enzyme recognition site. Similarly, the IS6110 target sequence alone may be amplified using $S_g$ and $S_{tb}$ with the $A_{tb}$ adapter primer, or using $S_{tb}$ and an $A_{tb}$ adapter primer modified to function as an amplification primer by replacing the M.g adapter sequence with a HincII restriction enzyme recognition site.

The amplification products of the IS6110, 16S and internal control target sequences may be detected by hybridization to oligonucleotide probes tagged with a detectable label, each one of three probes specifically hybridizing to one of the targets. If the target-specific and control-specific probes are hybridized simultaneously to the amplification products, the labels should be separately identifiable to facilitate distinguishing the respective amounts of control and target. Otherwise, separate aliquots of the amplification reaction may be separately hybridized to target-specific and control-specific probes tagged with the same label. The detectable label may be conjugated to the probe after it is synthesized or it may be incorporated into the probe during synthesis, for example in the form of a label-derivatized nucleotide. Such labels are known in the art and include directly and indirectly detectable labels. Directly detectable labels produce a signal without further chemical reaction and include such labels as fluorochromes, radioisotopes and dyes. Indirectly detectable labels require further chemical reaction or addition of reagents to produce the detectable signal. These include, for example, enzymes such as horseradish peroxidase and alkaline phosphatase, ligands such as biotin which are detected by binding to label-conjugated avidin, and chemiluminescent molecules. The probes may be hybridized to their respective amplification products in solution, on gels, or on solid supports. Following hybridization, the signals from the associated labels are developed, detected and separately quantitated using methods appropriate for the selected label and hybridization protocol. The amount of signal detected for each amplification product is a reflection of the amount present.

One preferred method for detecting the target and control amplification products is by polymerase extension of a primer specifically hybridized to the target or control sequence. The primer is labeled as described above, preferably with a radioisotope, so that the label of the primer is incorporated into the extended reaction product. This method is described in more detail by Walker, et al. (1992) *Nuc. Acids Res.* and PNAS, supra. A second preferred method for detecting amplified target and control sequences is a chemiluminescent method in which amplified products are detected using a biotiniylated capture oligodeoxynucleotide probe and an enzyme-conjugated detector oligodeoxynucleotide probe as illlustrated in Example 3. After hybridization of these two probes to different sites on an amplified target sequence, the complex is captured on a streptavidin-coated microtiter plate, and the chemiluminescent signal is developed and read in a luminometer. This detection method can be performed in less than two hours and is sensitive enough to detect as few as one pre-amplification target sequence.

SDA reactions employing the primers of the invention may incorporate thymine as taught by Walker, et al., supra, or they may wholly or partially substitute 2'-deoxyuridine 5'-triphosphate for TTP in the reaction (as shown in the instant Examples) as a means for reducing cross-contamination of subsequent SDA reactions as taught in U.S. Ser. No. 08/060,842. dU is incorporated into amplification products of both target and control sequences and can be excised by treatment with uracil DNA glycosylase (UDG). These abasic sites render the amplification product unamplifiable in subsequent SDAs. The internal control sequence as initially synthesized may also incorporate dU in place of thymine to prevent its amplification in subsequent SDAs. For example, SEQ ID NO: 12 is shown in the attached Sequence Listing as containing thymine but it may also consist of the corresponding sequence in which thymine is replaced wholly or paratially by dU. UDG may be inactivated by uracil DNA glycosylase inhibitor (Ugi) prior to performing the subsequent amplification to prevent excision of dU in newly-formed amplification products.

As certain of the primers and probes disclosed herein and exemplified in the following Examples are identical in sequence to primers and probes previously disclosed in the parent applications, the following correspondence of Sequence ID Nos. is provided for clarity:

| SEQ ID NO: IN- | CORRESPONDING SEQ ID NO: IN- | | FUNCTION |
|---|---|---|---|
| Instant Application | U.S. Ser. No. 08/073,197 | U.S. Ser. No. 08/058,648 | |
| 1 | 2 | None | IS6110 Amplification Primer |
| 2 | 10 | None | IS6110 Adapter Primer |
| 3 | 5 | None | IS6110 Bumper Primer |
| 4 | 6 | None | IS6110 Bumper Primer |
| 5 | 3 | None | 16S Amplification Primer |
| 6 | 9 | None | 16S Adapter Primer |
| 7 | 7 | None | 16S Bumper Primer |
| 8 | 8 | None | 16S Bumper Primer |
| 9 | None | None | M.tb Detector (Primer Ext.) |
| 10 | None | None | 16S Detector (Primer Ext.) |
| 11 | None | None | 16S Detector (Primer Ext.) |
| 12 | None | None | Internal Control Sequence |
| 13 | None | 6 | IS6110 Capture |
| 14 | None | 7 | IS6110 Detector (Hyb.) |
| 15 | None | 4 | Internal Control Capture |
| 16 | None | 5 | Int. Control Detector (Hyb.) |
| 17 | None | None | 16S Capture |
| 18 | None | None | 16S Detector (Hybridization) |
| 19 | None | None | 16S Detector -fc (Hyb.) |

The primers and/or probes for performing the assay methods of the invention may be packaged in the form of a diagnostic kit for simultaneous genus-specific and species-specific amplification of Mycobacterium DNA. The kits may comprise the amplification, adapter and bumper primers for genus-specific and species-specific amplification of Mycobacterium DNA as well as the reagents required for performing the SDA reaction (e.g., deoxynucleoside triphosphates, nicking restriction enzymes, buffers, exo⁻ polymerase, etc.). The kits may further optionally include the probes or primers useful for detecting and identifying the amplification products and/or an internal control sequence for co-amplification with the Mycobacterium target sequences.

EXAMPLE 1

This experimental example demonstrates coamplification of genus- and species-specific target nucleic acids using the amplification method illustrated in FIG. 1. The first target was the IS6110 insertion element of *M. tuberculosis* (target A). The second target was the 16S ribosomal gene of *M. tuberculosis* (target B). An amplification reaction was set up for each of the following species: *M. tuberculosis* H37Rv (ATCC 27294), *M. bovis* (CDC 81), *M. bovis*-BCG (CDC34), *M. avium* (ATCC 25291), *M. intracellulare* (ATCC 13950), *M. kansasii* (LCDC 711), *M. gastri* (LCDC 1301), *M. fortuitum* (LCDC 2801), *M. paratuberculosis* (LINDA), *M. chelonae* (TMC 1543), *M. malmoense* (CDC 93), *M. szulgai* (TMC 1328), *M. flavescens* (LCDC 2601), *M. xenopi* (LCDC 1901), *M. terrae* (TMC 1450), *M. marinum* (LCDC 801) and *M. gordonae* (TMC 1318). The "no target" sample contained no bacterial target DNA. The "no target" sample represented a control reaction to which no amplification enzymes were added.

SDA was performed generally as described by Walker, et al., *Nuc. Acids Res.*, supra, substituting dUTP for TTP to allow removal of contaminating amplicons. The final concentrations of components was 45 mM K$_i$PO$_4$, pH 7.5, 6 mM MgCl$_2$, 0.5 mM dUTP, 0.2 mM dGTP, 0.2 mM dCTP, 0.2 mM dATPαS, 0.1 mg/mL acetylated BSA, 12% (v/v) dimethylsulfoxide, 3% (v/v) glycerol (supplied by the stock solutions of exo⁻ klenow and HincII), 50 ng human placental DNA, 2.5 units exo⁻ klenow (United States Biochemical, Cleveland, Ohio), 150 units HincII (New England Biolabs, Beverly, Mass.), and 1000 genomes (molecules) of the Mycobacterium species being tested. Each sample contained two sets of four primers, as follows: Set #1) 500 nM of SEQ ID NO: 1 (S$_{tb}$ in FIG. 1), 50 nM of SEQ ID NO: 2 (A$_{tb}$), 25 nM of each of SEQ ID NO: 3 (B$_{tb1}$) and SEQ ID NO: 4 (B$_{tb2}$); Set #2 ) 500 nM of SEQ ID NO: 5 (S$_g$ in FIG. 1); 50 nM of SEQ ID NO: 6 (A$_g$), 25 nM of each of SEQ ID NO: 7 (B$_{g1}$) and SEQ ID NO: 8 (B$_{g2}$).

The primers of Set #1 are for species-specific detection of the IS6110 element. The IS6110 amplification primer (S$_{tb}$) is complementary to nucleotides 972–984 of the IS6110 sequence. The bumper primers in this example are complementary to nucleotides 954–966 and 1032–1044 of the IS6110 sequence respectively, however, other bumper primers which can be hybridized and extended to displace the extension product of the Set #1 amplification primer may be selected based on knowledge of the IS6110 sequence. The primers of Set #2 are for genus-specific detection of clinically relevant Mycobacteria.

Each 47 µL sample was assembled to contain all reagents except exo⁻ klenow and HincII using 10X concentrated stock solutions of each reagent. The MgCl$_2$ was added after addition and mixing of all other reagents (except exo⁻ klenow and HincII to prevent precipitation which occurs when K$_i$PO$_4$, dimethylsulfoxide and MgCl$_2$ are mixed at concentrations considerably higher than 45 mM, 12% (v/v) and 6 mM, respectively. The samples were then heated for 2 min. in a boiling water bath to denature the Mycobacterial DNA. A precipitate was observed immediately after removal from the boiling water bath. Incubating for 2 min. at 40° C. and mixing on a vortex mixer redissolved the majority of the high temperature precipitate. Exo⁻ klenow (1 µL of a 2.5 units/µL stock solution) and HincII (2 µL of a 75 units/µL stock solution) were added for a total sample volume of 50 µL, and the samples were incubated for 2 hr. at 40° C.

Amplification products were detected by primer extension as described by Walker, et al., *Nuc. Acids Res.*, supra, also substituting dUTP. A 5 µL aliquot of each sample was mixed with 5 µL of 45 mM K$_i$PO$_4$, pH 7.5, 6 mM MgCl$_2$, 0.5 mM dUTP, 0.2 mM dGTP, 0.2 mM dCTP, 0.2 mM dATPαS, 0.1 mg/mL acetylated BSA and 2 µL of a 5'-$^{32}$P detector probe stock solution (50 mM Tris-HCl, pH 8, 10 mM MgCl$_2$, 1 µM of each of the three 5'-$^{32}$P detector probes). The detector probe for the IS6110 target was SEQ ID NO: 9 (species-specific for M.tb complex). The detector probes for the 16S target were SEQ ID NO: 10 and SEQ ID NO: 11. SEQ ID NO: 11 corresponds to the 16S sequences of *M. fortuitum*, *M. chelonae*, *M. terrae*, *M. marinum* and *M. flavescens* ("fc" detector). SEQ ID NO: 10 corresponds to the remaining non-M.tb complex species tested. The 12 µL samples were then heated 1 min. in a boiling water bath. After incubating 2 min. at 37° C., 2 µL of 1 unit/µL of exo⁻ klenow were added and the samples were incubated for 15 min. at 37° C., followed by addition of 14 µL of 50% urea in 0.5X TBE.

Figure 3:
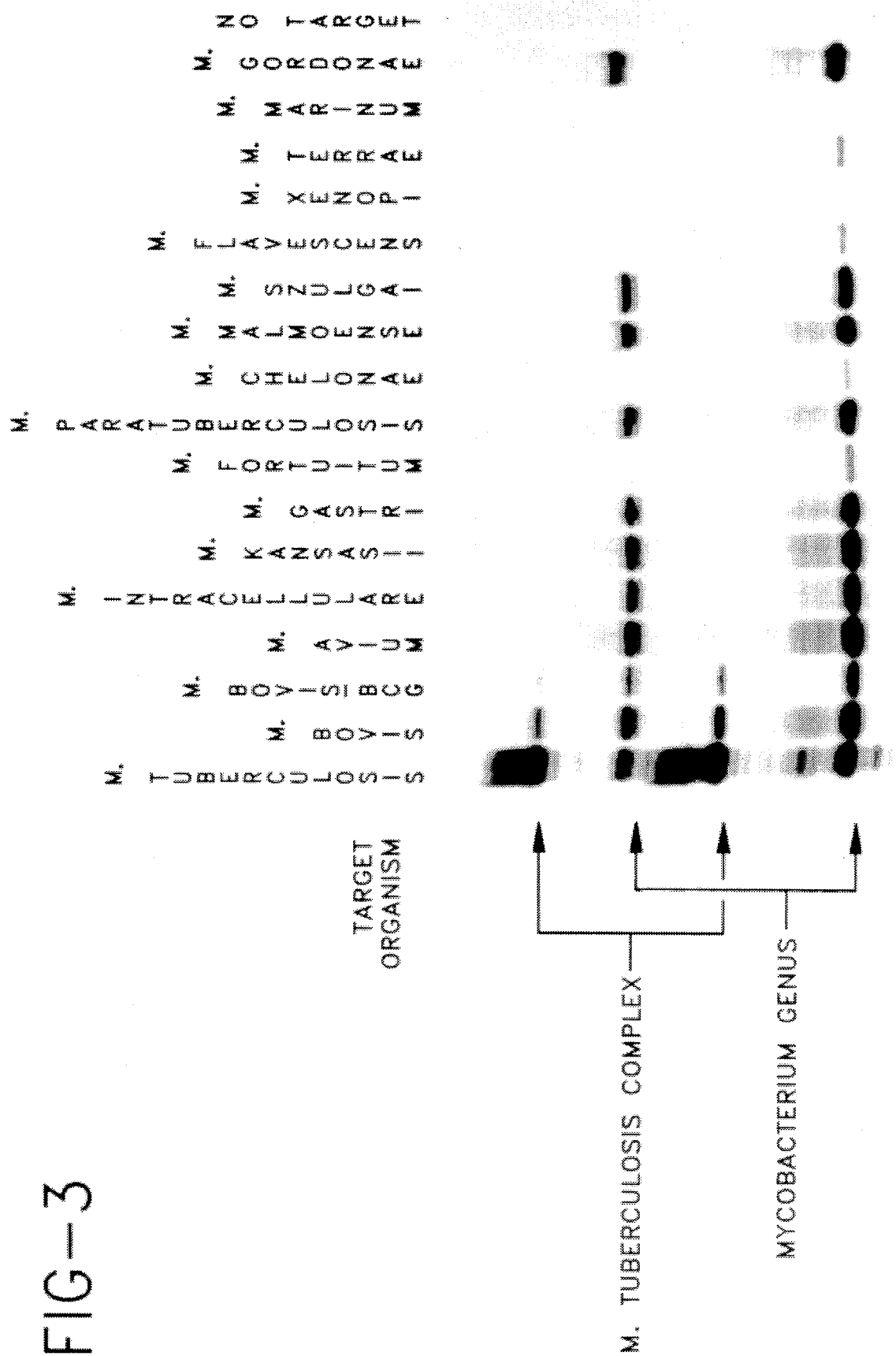
FIG. 3 is an autoradiograph showing the results of the experiment in Example 1.

Samples were heated for 1 min. at 95° C. and analyzed using 8% denaturing gel electrophoresis and autoradiography (Maniatis, et al. 1982. *Molecular Cloning: A Laboratory Manual* Cold Spring Harbor Laboratory, Cold Spring Harbor, N.Y.). The results are shown in FIG. 3. Amplified IS6110 (M.tb target) is indicated by extension of the SEQ ID NO: 9 detector probe to a 41- and 63-mer. Amplified 16S (M.g target) is indicated by extension of the SEQ ID NO: 10 and SEQ ID NO: 11 detector probes to a 30- and 51-mer.

As shown in FIG. 3, positive IS6110 and 16S signals were obtained for *M. tuberculosis*, *M. bovis* and *M. bovis*-BCG, all of which are members of the *M. tuberculosis* complex. For *M. tuberculosis*, the IS6110 signals were stronger than the 16S signals because this organism contains about 10 copies of the IS6110 element compared with a single copy of the 16S ribosomal gene. Roughly equivalent IS6110 and 16S signals were obtained with *M. bovis* and *M. bovis*-BCG because they contain one to two copies of the IS6110 element and a single copy of the 16S ribosomal gene. IS6110 signals were not seen for any Mycobacterium species tested which was not a member of the M.tb complex.

16S signals only were detected for *M. avium*, *M. intracellulare*, *M. kansasii*, *M. gastri*, *M. paratuberculosis*, *M. malmoense*, *M. szulgai* and *M. gordonae*, which have 16S target sequences identical to that of *M. tuberculosis*. *M. gordonae* is not normally pathogenic, but is a common contaminant in clinical laboratories. It is therefore possible that contamination of a negative sample with *M. gordonae* would produce a false positive result for the Mycobacterium genus in this test, as it does in culture-based tests. Relatively weak 16S signals were obtained for *M. fortuitum*, *M. chelonae*, *M. marinum* and *M. terrae*. It is possible that this result is related to a T—G mismatch which adapter SEQ ID NO: 6 forms in these species (see FIG. 2). However, the same experiment performed using a genus-specific adapter primer with a perfect match still produced a relatively weak signal, raising the possibility that the 16S gene of these species contains secondary structure which attenuates amplification. The signal obtained for *M. flavescens* was as strong as that for *M. fortuitum* despite an additional A—C mismatch at the 3'-end of adapter SEQ ID NO: 6. No 16S signal was obtained for *M. xenopi*, possibly due to a poor match with the detector probes. Based on these results, positive 16S signals would also be expected for Mycobacterium species in addition to those tested (e.g., *M. scrofulaceum*, *M. leprae*, *M. ulcerans*, *M. hemophilum* and *M. asiaticum*), as the 16S sequences of these species also match that of M.tb.

EXAMPLE 2

Figure 4:
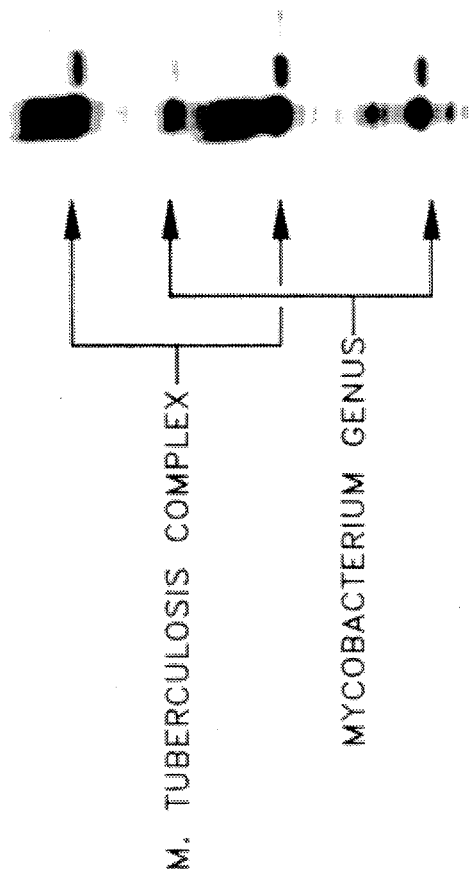
FIG. 4 is an autoradiograph showing the results of the experiment in Example 2.

This experimental example demonstrates the lack of cross-reactivity of the coamplification method with non-Mycobacteria. The amplifications and analyses were performed as in Example 1, except that target DNA was taken from either *M. tuberculosis* H37Rv (ATCC 27294) or the following non-Mycobacterium species: *Corynebacteria diphtheriae* (ATCC 11913), *Corynebacteria xerosis* (ATCC 373), *Corynebacteria pseudodiphtheriticum* (ATCC 10700), *Nocardia asteroides* (ATCC 3308), *Nocardia brasiliensis* (ATCC 19296), *Nocardia orientalis* (ATCC 19795), *Streptomyces somaliensis* (ATCC 33201), *Streptomyces griseus* (ATCC 10137), *Streptomyces albus* (ATCC 3004), *Streptomyces gedanensis* (ATCC 4880), *Actinomyces israelii* (ATCC 10049), *Eubacterium lentum* (ATCC 43055), *Rhodococcus equi* (ATCC 6939), *Rhodococcus rhodochrous* (ATCC 13808), *Propionibacterium acnes* (ATCC 6919),

*Actinoplanes auranticolor* (ATCC 15330), *Streptosporangium virialbum* (ATCC 33328), and *Streptoverticillium alboverticillatum* (ATCC 29818). Different species of the same genus were pooled together in one SDA sample as represented under the genus name. The number of *M. tuberculosis* genomes present in each SDA reaction is indicated in FIG. 4. The non-Mycobacterium samples contained $10^5$ genome copies of each indicated species. The "no target" sample did not contain bacterial DNA. The $^{32}$-p bands corresponding to amplification products for the IS6110 target (*M. tuberculosis* complex) and the 16S target (Mycobacterium genus) are indicated in FIG. 4.

All non-Mycobacterium organisms tested ($10^5$ genomes) produced signals weaker than the signal obtained for only 10 genomes of *M. tuberculosis*, even though the non-Mycobacterium organisms tested were generally similar to Mycobacterium.

EXAMPLE 3

This experimental example illustrates the embodiment of the invention in which an internal control sequence is co-amplified with the IS6110 and 16S target sequences using the IS6110/16S amplification primer pair (triplex amplification). The amplifications were performed as in Example 1 using M.tb DNA diluted to varying extents to assess the sensitivity of the detection methods. The amplification products were detected in a solid-phase chemiluminescent assay in which amplified target and control sequences were captured on microwell plates by hybridization to an immobilized capture probe. hybridization was detected by sandwich hybridization of the captured target or control sequence to a detector probe labeled with alkaline phosphatase. The capture probes were labeled at either the 5' or 3' end with biotin and immobilized by binding to streptavidin on the microwell plate. The detector probes were labeled at either the 5' or 3' end with alkaline phosphatase (AP) and detected by enzymatic reaction with LUMIPHOS 530 (Lumigen, Inc., Detroit, Mich.).

Oligodeoxynucleotide capture probes with 5' biotinylation (SEQ ID NO: 13 for the IS6110 target sequence and SEQ ID NO: 15 for the internal control sequence) were synthesized as described in Example 2 of U.S. Ser. No. 08/058,648. Oligodeoxynucleotide detector probes 3' labeled with AP (SEQ ID NO: 14 for IS6110 and SEQ ID NO: 16 for the internal control) were also synthesized and labeled as in U.S. Ser. No. 08/058,648.

Preparation of 3'-Biotinylated Capture Oligodeoxynucleotides

Oligodeoxynucleotide capture probes with 3' biotinylation were synthesized as follows. SEQ ID NO: 17 (capture probe for the 16S target sequence) was synthesized using a DNA synthesizer (Model 380B, Applied Biosystems, Foster City, Calif.). 3'BIOTIN-ON CPG (controlled pore glass, Clonetech, Palo Ako, Calif.) was used to attach a biotin moiety at the 3' terminus of the oligodeoxynucleotide. Two additional biotins were then added to the 3' terminus using BIOTIN-ON phosphoramidite reagent (also from Clonetech). The oligodeoxynucleotides were then prepared using standard phosphoramidite reagents and cleaved from the solid phase to give crude: 3'-biotinylated oligodeoxynucleotides. Purification was done by reverse phase High Pressure Liquid Chromatography (HPLC) (Brownlee Lab Aquapore RP 300 Column—220×4.6 mm, C8 column 7 particle, 300 Å pore size) with a UV monitor at 254 nm and a gradient of 14 to 44% Buffer B over one hour (Buffer B: 0.1M Triethylamine-Acetate pH 7 with 50% Acetonitrile; Buffer A: 0.1M Triethylamine-Acetate, pH 7) and a flow rate of 1 ml/minute.

Preparation of 5'-Alkaline Phosphatase Detector Oligodeoxynucleotides

Oligodeoxynucleotide detector probes for 5' labeling with alkaline phosphatase were synthesized from 5'-amino-oligodeoxynucleotides prepared using a DNA synthesizer (Model 380B, Applied Biosystems, Foster City, Calif.). SEQ ID NO: 19 is the detector probe for the 16S target sequence in *M. fortuitum*, *M. chelonae*, *M. terrae* and *M. flavescens* ("fc" detector). SEQ ID NO: 18 is the detector probe for the 16S target sequence in the remaining non-M.tb species of Mycobacteria tested. The reagent AMINOLINK II (Applied Biosystems, Foster City, Calif.) was used to place an amine group on the 5'-ends of the oligodeoxynucleotides for subsequent conjugation with alkaline phosphatase as described above. The crude conjugates were dialyzed into 20 mM Tris pH 7.5 and concentrated using a CENTRIPREP 30 (Amicon, Danvers, Mass.) to approximately 2 ml. The concentrated conjugated were then purified by HPLC using a DEAE-5PW column (7.5 mm×7.5 cm) and a gradient of 0 to 66% Buffer B (Buffer B: 20 mM Tris, 1M NaCl pH 7.5, Buffer A: 20 mM Tris pH 7.5) and a flow rate of 1 ml/minute. Absorbance was monitored at 254 nm. The fractions were collected, the activity of the conjugate was determined, and the conjugated were stored as described above.

Preparation of Coated Microwell Plates

Biotinylated bovine serum albumin (biotin*BSA) (Pierce, Rockford, Ill.) was diluted to 5 µg/ml in 50 mM carbonate pH 9.6 (Sigma, St. Louis, Mo., prepared using autoclaved water) and was pipetted into each well (100 µl/well) of Labsystems strip wells (Labsystems, Research Triangle Park, N.C.), and incubated at room temperature overnight. The plates were washed twice (375 µl/wash) using FTA hemagglutination buffer pH 7.2 (Becton Dickinson Microbiology Systems, Cockeysville, Md.) prepared using autoclaved water. Streptavidin in hemagglutination buffer was added to the biotin*BSA coated wells (100 µl/well). Plates were covered and incubated overnight at room temperature. Unbound streptavidin was discarded by inversion of the wells and blocking buffer (300 µl/well—hemagglutination buffer pH 7.2, 0.05% w/v BSA) was added. The plates were covered and incubated overnight as above, the blocking buffer was discarded by inversion of the wells. Plates were washed twice with hemagglutination buffer (375 µl/well), then once using hemagglutination buffer with 2% w/v trehalose (375 µl/well—Fluka, Ronkonkoma, N.Y.). Plates were dried for 1 hour at 37° C., sealed in mylar pouches with desiccant, and stored overnight at room temperature prior to use. The plates were stored thereafter at 2°–8° C.

Microwell Assay Procedure

SDA was performed as in Example 1 on samples containing 0, 5, 10,20, 40 and 80 copies of the M.tb genome. A "heat killed" sample was also included to assess the background luminescence generated by the detector probe. The heat killed sample was heated immediately upon beginning the SDA reaction to prevent amplification. Each reaction also contained 1000 copies of the internal control sequence (SEQ ID NO: 12 in which thymine is replaced by dU). Forty-five µl of each completed SDA reaction was diluted into 180 µl of sterile water in a sterile siliconized tube. The diluted SDA reactions were heated to 95° C. for 3 min. to denature the DNA. Tubes were cooled for 5 min. at room temperature and then 50 µl of each denatured, diluted SDA reaction was added to each of three wells. In one well the SDA reaction products were hybridized with the IS6110 capture and detector probe set, in the second well the SDA reaction products were hybridized with the 16S capture and detector probe set and in the third well the SDA reaction products were hybridized with the internal control capture and detector probe set. Immediately after addition of the sample to the well, 50 μl/well of hybridization mix (100 mM sodium phosphate, 0.02% BSA, 1.8M NaCl, 0.2% NaN$_3$, 0.1 mM ZnCl$_2$, 20 μg/ml sheared salmon sperm DNA, pH 7.0, capture and detector probes) was added. The plate was covered and incubated for 45 min. at 37° C. Three stringency washes (300 μl/well—10 mM Tris pH 7.5, 0.1% w/v BSA, 0.01% v/v NONIDET P-40, 250 mM NaCl) were performed at room temperature. Each wash was allowed to remain in the wells for 1 min. before removing. LUMIPHOS 530 AP substrate (100 μl/well) was added and the plates were covered and incubated for 30 min. at 37° C. Luminescence (Relative Light Units—RLU) was read on a microtiter plate luminometer (Labsystems, Research Triangle Park, N.C.) at 37° C., using a 2 second/well integration time.

The results, in RLU, are shown in the following table. "Over" indicates an RLU reading above the maximum recordable by the instrument.

| GENOMES | SPECIES-SPECIFIC (IS6110) | GENUS-SPECIFIC- (16S) | INTERNAL CONTROL |
|---|---|---|---|
| 0 | 11 | 12 | 8515 |
| 5 | 300 | 68 | Over |
| 10 | 945 | 164 | 7744 |
| 20 | 3157 | 615 | Over |
| 40 | 3618 | 694 | 14118 |
| 80 | 6890 | 1367 | Over |
| Heat Killed | 5 | 18 | 3 |

The assay detected as little as five genomic copies of 16S rDNA and 5 genomic copies of IS6110 from M.tb above background. Amplification activity, as evidenced by the high levels of amplification of the internal control sequence, was high in each sample, i.e., the samples were not inhibitory to the amplification reaction.

---

What is claimed is:

1. A method for simultaneously amplifying multiple Mycobacterium target sequences in a sample comprising:
    a) hybridizing a first primer consisting of SEQ ID NO: 1 to the target sequences, extending the first primer with polymerase to produce a first extension product and displacing the first extension product;
    b) hybridizing a second primer consisting of SEQ ID NO: 2 to the first extension product, extending the second primer to produce a second extension product and displacing the second extension product;
    c) hybridizing a third primer consisting of SEQ ID NO: 5 to the target sequences, extending the third primer with polymerase to produce a third extension product and displacing the third extension product;
    d) hybridizing a fourth primer consisting of SEQ ID NO: 6 to the third extension product, extending the fourth primer with polymerase to produce a fourth extension product and displacing the fourth extension product, and;
    e) simultaneously amplifying the second and fourth extension products in a Strand Displacement Amplification reaction using; SEQ ID NO: 1 and SEQ ID NO: 5 as amplification primers.

2. The method of claim 1 further comprising detecting amplification products of step (e) as an indication of presence or absence of *Mycobacterium tuberculosis* complex species or species of the genus Mycobacterium in the sample.

3. The method of claim 2 wherein the first, second, third or fourth extension product is displaced by extension of a bumper primer.

4. The method of claim 3 wherein the bumper primer consists of SEQ ID NO: 3, SEQ ID NO: 4, SEQ ID NO: 7 or SEQ ID NO: 8.

5. The method of claim 3 wherein the first and third primers are present in approximately 10-fold excess over the third and fourth primers.

6. The method of claim 2 wherein the second and fourth extension products are amplified using a restriction enzyme selected from the group consisting of HincII, HindII, AvaI, NciI and Fnu4HI.

7. The method of claim 2 wherein the amplification products are detected by hybridization and extension of a $^{32}$P-labeled primer.

8. The method of claims 1 or 2 further comprising the steps of:
    a) hybridizing the second primer to a second strand of the target sequences, extending the second primer with polymerase to produce a fifth extension product and displacing the fifth extension product;
    b) hybridizing the first primer to the fifth extension product, extending the first primer with polymerase to produce a sixth extension product and displacing the sixth extension product;
    c) hybridizing the fourth primer to a second strand of the target sequences, extending the fourth primer with polymerase to produce a seventh extension produce and displacing the seventh extension product;

d) hybridizing the third primer to the seventh extension product, extending the third primer with polymerase to produce an eighth extension product and displacing the eighth extension product, and;

e) simultaneously amplifying the sixth and eighth extension products in a Strand Displacement Amplification reaction using SEQ ID NO: 1 and SEQ ID NO: 5 as amplification primers.

9. A method for simultaneously amplifying multiple Mycobacterium target sequences and an internal control sequence in a sample comprising:

a) adding an internal control sequence consisting of SEQ ID NO: 12 to the sample;

b) hybridizing a first primer consisting of SEQ ID NO: 1 to the target sequences, extending the first primer with polymerase to produce a first extension product and displacing the first extension product;

b) hybridizing a second primer consisting of SEQ ID NO: 2 to the first extension product, extending the second primer to produce a second extension product and displacing the second extension product;

c) hybridizing a third primer consisting of SEQ ID NO: 5 to the target sequences, extending the third primer with polymerase to produce a third extension product and displacing the third extension product;

d) hybridizing a fourth primer consisting of SEQ ID NO: 6 to the third extension product, extending the fourth primer with polymerase to produce a fourth extension product and displacing the fourth extension product, and;

e) simultaneously amplifying the second and fourth extension products and the internal control sequence in a Strand Displacement Amplification reaction using SEQ ID NO: 1 and SEQ ID NO: 5 as amplification primers.

10. The method of claim 9 further comprising detecting the amplification products of step (e) as an indication of presence or absence of *Mycobacterium tuberculosis* complex species or species of the genus Mycobacterium in the sample.

11. The method of claim 10 wherein the first, second, third or fourth extension product is displaced by extension of a bumper primer.

12. The method of claim 11 wherein the bumper primer consists of SEQ ID NO: 3, SEQ ID NO: 4, SEQ ID NO: 7 or SEQ ID NO: 8.

13. The method of claim 11 wherein the first and third primers are present in approximately 10-fold excess over the third and fourth primers.

14. The method of claim 10 wherein the second and fourth extension products are amplified using a restriction enzyme selected from the group consisting of HincII, HindII, AvaI, NciI and Fnu4HI.

15. The method of claim 10 wherein the amplification products are detected in a chemiluminescent assay by hybridization to an alkaline phosphatase-labeled detector probe.

16. The method of claims 9 or 10 further comprising the steps of:

a) hybridizing the second primer to a second strand of the target sequences, extending the second primer with polymerase to produce a fifth extension product and displacing the fifth extension product;

b) hybridizing the first primer to the fifth extension product, extending the first primer with polymerase to produce a sixth extension product and displacing the sixth extension product;

c) hybridizing the fourth primer to a second strand of the target sequences, extending the fourth primer with polymerase to produce a seventh extension produce and displacing the seventh extension product;

d) hybridizing the third primer to the seventh extension product, extending the third primer with polymerase to produce an eighth extension product and displacing the eighth extension product, and;

e) simultaneously amplifying the sixth and eighth extension products in a Strand Displacement Amplification reaction using SEQ ID NO: 1 and SEQ ID NO: 5 as amplification primers.

17. An oligonucleotide consisting of a sequence selected from the group consisting of SEQ ID NO: 1, SEQ ID NO: 2, SEQ ID NO: 5 and SEQ ID NO: 6.

18. An oligonucleotide consisting of SEQ ID NO: 12.

19. An oligonucleotide consisting of a nucleotide sequence selected from the group consisting of SEQ ID NO: 13, SEQ ID NO: 14, SEQ ID NO: 15, SEQ ID NO: 16, SEQ ID NO: 17, SEQ ID NO: 18 and SEQ ID NO: 19.

20. The oligonucleotide of claim 19 which is conjugated to a label.

21. The oligonucleotide of claim 20 wherein the label is alkaline phosphatase or biotin.

22. A method for genus-specific amplification of Mycobacterium target sequences in a sample comprising:

a) hybridizing a first primer consisting of SEQ ID NO: 5 to the target sequences, extending the first primer with polymerase to produce a first extension product and displacing the first extension product;

b) hybridizing a second primer consisting of SEQ ID NO: 6 to the first extension product, extending the second primer to produce a second extension product and displacing the second extension product, and;

e) amplifying the second extension product in a Strand Displacement Amplification reaction using SEQ ID NO: 1 and SEQ ID NO: 5 as amplification primers.

23. The method of claim 22 further comprising simultaneous amplification of an internal control sequence consisting of SEQ ID NO: 12 and the second extension product.

24. The method of claim 22 further comprising the steps of:

a) hybridizing the second primer to a second strand of the target sequences, extending the second primer with polymerase to produce a third extension product and displacing the third extension product;

b) hybridizing the first primer to the third extension product, extending the first primer with polymerase to produce a fourth extension product and displacing the fourth extension product, and;

c) amplifying the fourth extension product in a Strand Displacement Amplification reaction using SEQ ID NO: 1 and SEQ ID NO: 5 as amplification primers.

25. A kit for amplifying Mycobacterium target sequences comprising:

a) a first oligonucleotide consisting of SEQ ID NO: 1, a second oligonucleotide consisting of SEQ ID NO: 2, a third oligonucleotide consisting of SEQ ID NO: 5 and a fourth oligonucleotide consisting of SEQ ID NO: 6, and;

b) reagents for hybridizing the first, second, third and fourth oligonucleotides to the Mycobacterium target sequences, extending the oligonucleotides and displacing the oligonucleotides from the target sequences in an amplification reaction.

26. A kit for genus-specific amplification of Mycobacterium target sequences comprising:
   a) a first oligonuclectide consisting of SEQ ID NO: 5 and a second oligonucleotide consisting of SEQ ID NO: 6, and
   b) reagents for hybridizing the first and second oligonucleotides to the Mycobacterium target sequences, extending the oligonucleotides and displacing the oligonucleotides from the target sequences in an amplification reaction.

27. The kit of claims 25 or 26 further comprising an oligonucleotide consisting of SEQ ID NO: 12 as an internal control sequence for the amplification.

28. The kit of claim 27 further comprising an oligonucleotide for detection of amplified target sequences.

29. The kit of claim 28 wherein the oligonucleotide for detection of amplified target sequences comprises a nucleotide sequence consisting of SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18 or SEQ ID NO: 19.

30. The kit of claim 29 wherein the oligonucleotide for detection of amplified target sequences is conjugated to a label.

31. The kit of claim 30 wherein the label is alkaline phosphatase or biotin.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TTGAATAGTC GGTTACTTGT TGACGGCGTA CTCGACC 37

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTCGCGTTGT TCACTGAGAT CCCCT 25

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TGGACCCGCC AAC 13

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single (D) TOPOLOGY: linear (xi) SEQUENCE DESCRIPTION: SEQ ID NO:4:

CGCTGAACCG GAT　　　　　　　　　　　　　　　　　　　　　　　　　　　　　　　13

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

TTCTATAGTC GGTTACTTGT TGACGTCGCG TTGTTC　　　　　　　　　　　　　　　　　36

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

GGCGTACTCG ACCACGCTCA CAGTTA　　　　　　　　　　　　　　　　　　　　　　　26

(2) INFORMATION FOR SEQ ID NO:7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:7:

CGGAATTACT GGG　　　　　　　　　　　　　　　　　　　　　　　　　　　　　　　13

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:8:

AGTCTGCCCG TATC　　　　　　　　　　　　　　　　　　　　　　　　　　　　　　14

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:9:

TCCGTATGGT GGATA　　　　　　　　　　　　　　　　　　　　　　　　　　　　　15

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:10:

GCCGTGAGAT TTCAC        15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCTGTGAGTT TTCAC        15

( 2 ) INFORMATION FOR SEQ ID NO:12:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GACGGCGTAC TCGACCAGCG ACGATGTCTG AGGCAACTAG CAAAGCTGAA CAACGCGAC        59

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CCTGAAAGAC GTTAT        15

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCACCATACG GATAGT        16

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GCTTTGCTAG TTGCC        15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear -continued (x i) SEQUENCE DESCRIPTION: SEQ ID NO:16:

TCAGACATCG TCGCT                                                                                           15

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:17:

ACTGTGAGCG TGGTC                                                                                           15

(2) INFORMATION FOR SEQ ID NO:18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:18:

AAATCTCACG GCTTA                                                                                           15

(2) INFORMATION FOR SEQ ID NO:19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:19:

AAAACTCACA GCTTA                                                                                           15